US012594155B2

(12) United States Patent
Hanson et al.

(10) Patent No.: US 12,594,155 B2
(45) Date of Patent: Apr. 7, 2026

(54) PROXIMAL EMBOLIC PROTECTION DEVICE FOR CAROTID STENTING

(71) Applicant: Boston Scientific Scimed, Inc., Maple Grove, MN (US)

(72) Inventors: Cass Alexander Hanson, St. Paul, MN (US); Ryan Hendrickson, Albertville, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 57 days.

(21) Appl. No.: 18/653,034

(22) Filed: May 2, 2024

(65) Prior Publication Data

US 2024/0366358 A1 Nov. 7, 2024

Related U.S. Application Data

(60) Provisional application No. 63/463,674, filed on May 3, 2023.

(51) Int. Cl.
*A61F 2/01* (2006.01)
*A61B 17/12* (2006.01)
*A61M 25/10* (2013.01)

(52) U.S. Cl.
CPC .......... *A61F 2/014* (2020.05); *A61B 17/1204* (2013.01); *A61B 17/12109* (2013.01); *A61B 17/12136* (2013.01); *A61B 2017/1205* (2013.01)

(58) Field of Classification Search
CPC ............... A61F 2/014; A61B 17/12022; A61B 17/12036; A61B 17/12027;
(Continued)

(56) References Cited

U.S. PATENT DOCUMENTS 5,772,609 A 6/1998 Nguyen et al.
6,139,510 A 10/2000 Palermo
(Continued)

FOREIGN PATENT DOCUMENTS

EP 1409064 B1 12/2013

OTHER PUBLICATIONS

International Search Report and Written Opinion for International Application No. PCT/US2024/027372, dated Aug. 14, 2024. (16 pages).

*Primary Examiner* — Katherine M Shi
(74) *Attorney, Agent, or Firm* — Seager, Tufte & Wickhem, LLP

(57) ABSTRACT

A method of providing embolic protection for carotid stenting includes advancing an arterial sheath into a patient's arterial system and advancing a venous sheath into the patient's venous system. A fluid connection may be established between the venous sheath and the arterial sheath that enables retrograde blood flow through the arterial sheath. The arterial sheath may be advanced through the vasculature and into the patient's carotid artery, and an inflatable balloon may be inflated within the patient's carotid artery in order to occlude antegrade blood flow therethrough. An interventional tool may be advanced through the inner lumen of the arterial sheath, the interventional tool dimensioned such that a portion of the cross-sectional area of an inner lumen of the arterial sheath remains open for retrograde blood flow.

15 Claims, 7 Drawing Sheets

(58) Field of Classification Search
   CPC ........ A61B 17/12099; A61B 17/12109; A61B
                17/12131; A61B 17/12136; A61B
                17/1204; A61B 2017/1205; A61B
              2017/22067; A61M 2025/1052; A61M
           2025/1093; A61M 25/10; A61M 25/1002;
             A61M 2025/0681; A61M 2025/1061;
                                        A61M 1/3613
   See application file for complete search history.

(56)                    References Cited

U.S. PATENT DOCUMENTS

| | | | |
|---|---|---|---|
| 7,083,594 | B2 | 8/2006 | Coppi |
| 2002/0087119 | A1 | 7/2002 | Parodi |
| 2007/0060942 | A2 | 3/2007 | Zadno-Azizi |
| 2010/0030256 | A1* | 2/2010 | Dubrul ............... A61B 10/0266 |
| | | | 606/200 |
| 2018/0125502 | A1 | 5/2018 | Allen |
| 2021/0353399 | A1 | 11/2021 | Hilmy |
| 2022/0202552 | A1 | 6/2022 | MacDonald et al. |
| 2022/0313272 | A1 | 10/2022 | Pillai |

* cited by examiner

12

17

14

16

10

PROXIMAL EMBOLIC PROTECTION DEVICE FOR CAROTID STENTING

CROSS-REFERENCE TO RELATED APPLICATIONS

This application claims the benefit of priority under 35 U.S.C. § 119 of U.S. Provisional Application No. 63/463,674, filed May 3, 2023, the entire disclosure of which is hereby incorporated by reference.

TECHNICAL FIELD

The disclosure is directed to performing stenting within the carotid artery. More particularly, the disclosure is directed to providing embolic protection such as proximal embolic protection during carotid stenting.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

The disclosure is directed to several alternative designs, materials and methods of manufacturing medical device structures and assemblies, and the use thereof. An example may be found in a method of providing embolic protection for carotid stenting. The method includes advancing an arterial sheath into a patient's arterial system, the arterial sheath defining an inner lumen having a cross-sectional area of at least 5 square millimeters, the arterial sheath including an inflatable balloon. A venous sheath is advanced into the patient's venous system. A fluid connection is established between the venous sheath and the arterial sheath to enable retrograde blood flow through the arterial sheath. The arterial sheath is advanced through the patient's arterial system to a position within the patient's carotid artery. The inflatable balloon is inflated within the patient's carotid artery in order to occlude antegrade blood flow therethrough. An interventional tool is advanced through the inner lumen of the arterial sheath, the interventional tool having a maximum outer diameter within the inner lumen of the arterial sheath such that at least 40 percent of the cross-sectional area of the inner lumen remains open for retrograde blood flow even while the interventional tool remains within the inner lumen of the arterial sheath.

Alternatively or additionally, the inner lumen of the arterial sheath may have a cross-sectional area of at least 5.5 square millimeters.

Alternatively or additionally, the interventional tool may have a maximum outer diameter within the inner lumen of the arterial sheath of 2 millimeters Alternatively or additionally, the arterial sheath includes an inner shaft having an inner shaft wall thickness of about 0.1 millimeters, an outer shaft having an outer shaft wall thickness of about 0.1 millimeters, and an annular inflation lumen extending between the inner shaft and the outer shaft, the annular inflation lumen having a cross-sectional area in a range of 0.4 square millimeters to 0.5 square millimeters.

Alternatively or additionally, advancing the arterial sheath into the patient's arterial system may include accessing the patient's arterial system via the patient's femoral artery.

Alternatively or additionally, advancing the venous access sheath into the patient's venous system may include accessing the patient's venous system via the patient's femoral vein.

Alternatively or additionally, inflating the inflatable balloon within the patient's carotid artery may include inflating the inflatable balloon within the patient's common carotid artery.

Alternatively or additionally, only the patient's common carotid artery is occluded.

Another example may be found in a method of providing embolic protection for carotid stenting. The method includes advancing an arterial sheath into a patient's femoral artery, the arterial sheath defining an inner lumen having a diameter of at least 8 French (2.667 millimeters), the arterial sheath including an inflatable balloon. A venous sheath is advanced into the patient's femoral vein. A fluid connection is established between the venous sheath and the arterial sheath to enable retrograde blood flow through the arterial sheath. The arterial sheath is advanced through the patient's vasculature to a position proximate the patient's common carotid artery. The inflatable balloon is inflated within the patient's common carotid artery in order to occlude antegrade blood flow through the patient's common carotid artery.

Alternatively or additionally, the method may further include advancing a guidewire through the patient's femoral artery and through the patient's vasculature to a position beyond the patient's common carotid artery, and advancing the arterial sheath through the patient's vasculature to a position proximate the patient's common carotid artery may include advancing the arterial sheath over the guidewire with a dilator disposed within the arterial sheath and advancing over the guidewire.

Alternatively or additionally, the method may further include advancing an interventional tool through the inner lumen of the arterial sheath.

Alternatively or additionally, the interventional tool may have a maximum outer diameter of 6 French.

Alternatively or additionally, establishing a fluid connection between the venous sheath and the arterial sheath may include coupling a filter within a fluid path extending between the venous sheath and the arterial sheath.

Alternatively or additionally, establishing a fluid connection between the venous sheath and the arterial sheath may include coupling a flow control device within a fluid path extending between the venous sheath and the arterial sheath.

Alternatively or additionally, the method may include occluding the patient's common carotid artery without separately occluding the external carotid artery or the internal carotid artery.

Alternatively or additionally, the arterial sheath may include an inner shaft having an inner sheath wall thickness of about 0.1 millimeters, an outer shaft having an outer sheath wall thickness of about 0.1 millimeters, and an annular inflation lumen extending between the inner shaft and the outer shaft, the annular inflation lumen having a cross-sectional area in a range of 0.4 square millimeters to 0.5 square millimeters.

Another example may be found in an arterial embolic protection sheath. The arterial embolic protection sheath includes an elongate shaft having a length of at least 100 centimeters, the elongate shaft including an inner layer defining a lumen having an inner diameter of at least 8 French, an outer layer defining an outer surface having an outer diameter of at least 9 French, and an annular inflation lumen extending between the inner layer and the outer layer. An inflatable balloon is secured to the elongate shaft and is in fluid communication with the annular inflation lumen.

Alternatively or additionally, the inflatable balloon may have an inflated diameter in a range of 5 to 13 millimeters.

Alternatively or additionally, the inflatable balloon may be secured to the elongate shaft such that the inflatable balloon extends distally to a distal end of the elongate shaft.

Alternatively or additionally, the inflatable balloon may be secured to the elongate shaft such that the inflatable balloon extends distally beyond a distal end of the elongate shaft.

The preceding summary is provided to facilitate an understanding of some of the innovative features unique to the present disclosure and is not intended to be a full description. A full appreciation of the disclosure can be gained by taking the entire specification, claims, figures, and abstract as a whole.

BRIEF DESCRIPTION OF THE DRAWINGS

The disclosure may be more completely understood in consideration of the following description of various examples in connection with the accompanying drawings, in which.

Figure 1:
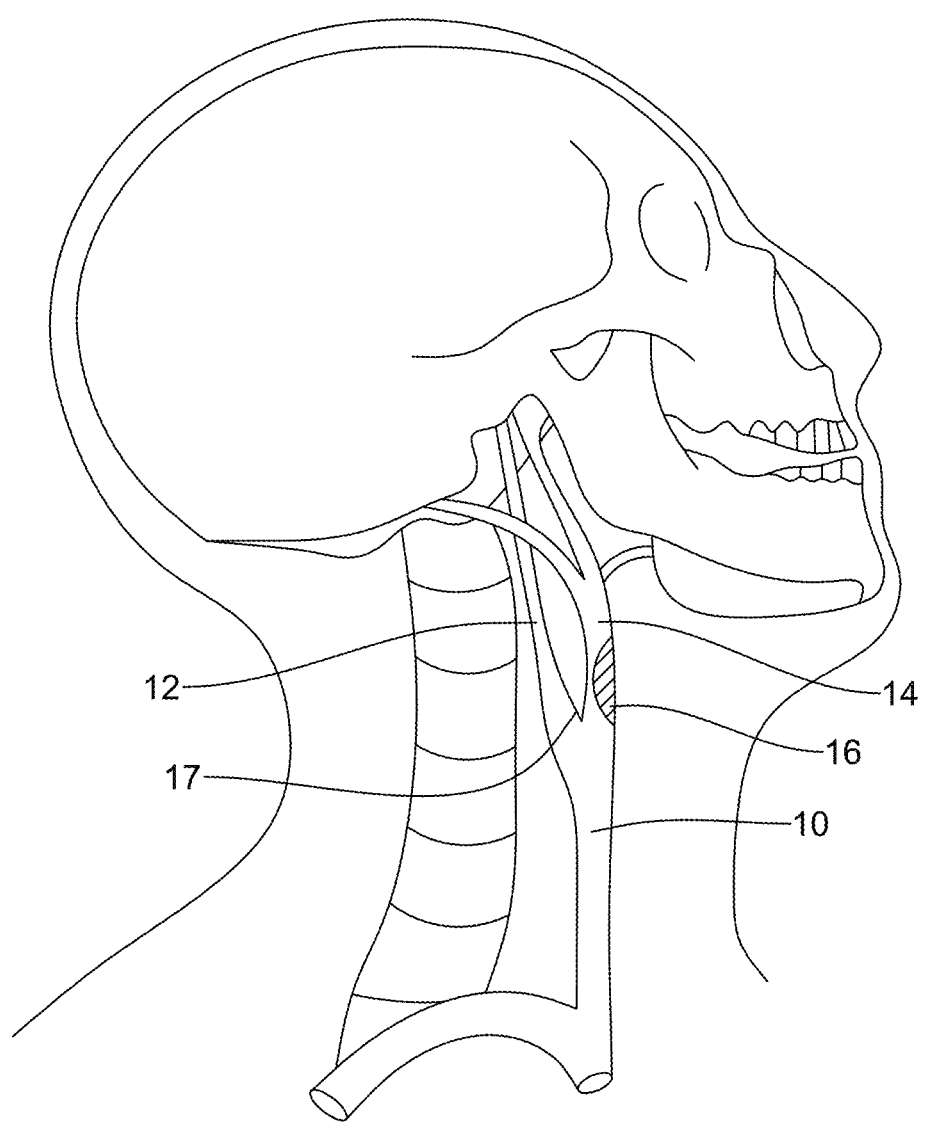
FIG. 1 is a partial cutaway view of a portion of a human head and neck, illustrating some of the vasculature within the neck.

While the disclosure is amenable to various modifications and alternative forms, specifics thereof have been shown by way of example in the drawings and will be described in detail. It should be understood, however, that the intention is not to limit the disclosure to the particular examples described. On the contrary, the intention is to cover all modifications, equivalents, and alternatives falling within the spirit and scope of the disclosure.

DESCRIPTION

The following description should be read with reference to the drawings, in which like elements in different drawings are numbered in like fashion. The drawings, which are not necessarily to scale, depict examples that are not intended to limit the scope of the disclosure. Although examples are illustrated for the various elements, those skilled in the art will recognize that many of the examples provided have suitable alternatives that may be utilized.

All numbers are herein assumed to be modified by the term "about", unless the content clearly dictates otherwise. The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is contemplated that the feature, structure, or characteristic may be applied to other embodiments whether or not explicitly described unless clearly stated to the contrary.

A variety of arterial diseases are known. Carotid Artery Disease (CAD) is an example of an arterial disease in which plaque lesions may develop within a patient's carotid artery. Because of the position of the carotid artery, and because the carotid artery normally carries oxygenated blood from the heart towards the brain, it will be appreciated that performing endovascular catheter procedures such as but not limited to carotid artery stenting within the carotid artery may cause particles dislodged from the lesion or lesions to flow upwards into the brain during the endovascular catheter procedures. Foreign material entering the brain may have deleterious effects on a patient. While distal protection devices may be used to help capture dislodged particles, it will be appreciated that such distal protection devices have to cross the lesion in order to reach a position distal of the lesion. The act of advancing and positioning a distal protection device may in itself dislodge particles from the lesion.

Proximal protection devices do not have to be advanced across the lesion. In some instances, a proximal protection device such as an arterial sheath may be advanced through a patient's arterial system to a point within the carotid artery. As an example, the proximal protection device may enter the arterial system via the femoral artery, although other access points are contemplated. In some instances, the proximal protection device may reach a point within the common carotid artery, which is proximal of where the common carotid artery bifurcates into the external carotid artery and the internal carotid artery. Inflating an inflatable balloon at the distal end of the arterial sheath can occlude anterograde blood flow through the common carotid artery. By fluidly coupling a proximal end of the arterial sheath with the venous sheath, and because of the pressure differences between the arterial system and the venous system, retrograde blood flow may be created. As a result, any particles or other debris that may be dislodged from the lesion during a process of advancing the arterial sheath through the vasculature as well as during any interventional process such as stenting, will flow backwards through the arterial sheath and through the venous sheath and into the venous system.

FIG. 1 is a partial cut-away view of the human head and neck, showing some of the vasculature. FIG. 1 shows a common carotid artery 10, which bifurcates into the external carotid artery 12 and the internal carotid artery 14. A lesion 16 is schematically shown within the internal carotid artery 14, just above a bifurcation point 17. An arterial sheath may be advanced up through the vasculature to a point within the common carotid artery 10 and an inflatable occlusion balloon carried by the arterial sheath may be used to occlude anterograde blood flow through the common carotid artery 10. The common carotid artery 10 may be reached by advancing through the arterial system to the common carotid artery 10. The arterial system may be accessed via a number of different arteries, but in some instances, the arterial system may be accessed via one of the patient's femoral arteries, as the patient has a femoral artery extending through the groin and down either leg. In some instances, other arteries providing a shorter path to the common carotid artery 10 may be utilized.

Figure 2:
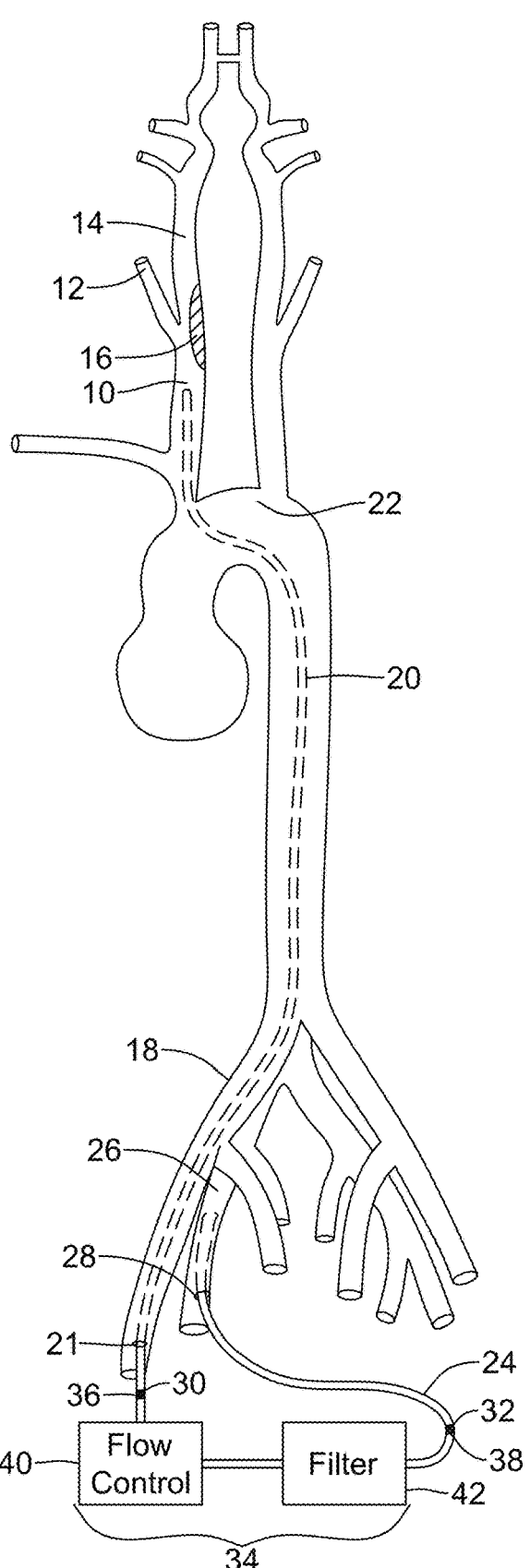
FIG. 2 is a schematic view of a portion of a human anatomy, including an illustrative flow path formed between an illustrative arterial sheath extending from the femoral artery to the carotid artery and a venous sheath extending from the femoral vein.

FIG. 2 is a schematic view of a portion of the patient's vasculature providing an illustrative path for advancing an arterial sheath from a femoral artery 18. An arterial sheath 20 is schematically seen, passing from an access point 21 within the femoral artery 18, through an aortic arch 22 and into the common carotid artery 10. A Seldinger technique may be used to create the access point 21 under fluoroscopic guidance. In some instances, a Seldinger technique involves introducing a needle into the vasculature, followed by advancing a wire through the needle and into the vein before the needle is withdrawn. The arterial sheath 20, along with an introducer, may be advanced over the wire and into the femoral artery 18. The arterial sheath 20 may subsequently be advanced through the vasculature to reach the common carotid artery 10, for example.

In some instances, either before or after the arterial sheath 20 has been introduced into the femoral artery 18, a venous sheath 24 may be introduced into the venous system. In some instances, this involves a femoral vein 26, although other access points to the venous system are contemplated. The venous sheath 24 may be introduced into the femoral vein 26 at an access point 28 in a manner similar to that used for introducing the arterial sheath 20 into the femoral artery 18. As an example, a Seldinger technique may be used under fluoroscopic guidance.

A proximal end 30 of the arterial sheath 20 and a proximal end 32 of the venous sheath 24 may be joined to a fluid path 34. In some instances, the fluid path 34 may simply represent one or more fittings or connections that allow the proximal end 30 of the arterial sheath 20 and the proximal end 32 of the venous sheath 24 to be fluidly coupled together. In some instances, the proximal end 30 of the arterial sheath 20 may include a fitting 36 and the proximal end 32 of the venous sheath 24 may include a fitting 38 that permits a direct connection between the proximal end 30 of the arterial sheath 20 and the proximal end 32 of the venous sheath 24.

In some instances, once the fluid path 34 between the arterial sheath 20 and the venous sheath 24 has been established, the arterial sheath 20 may be advanced further into the femoral artery 18 (or other artery if used) towards the common carotid artery 10. In some instances, the fitting 36 and the fitting 38 may each be adapted to be coupled with one or more additional components within the fluid path 34. As an example, in some instances the fluid path 34 may include a flow control device 40. The flow control device 40 may include an on/off valve that may be adjusted by an operator to either permit retrograde blood flow through the fluid path 34, or to prevent retrograde blood flow through the fluid path 34. In some instances, the flow control device 40 may be adapted to be able to adjust the relative retrograde blood flow through the fluid path 34, for example. In some instances, the fluid path 34 may include a filter 42. The filter 42 may be adapted to screen out any particles over a threshold diameter, for example. In some instances, the filter 42 may be adapted to screen out some particles, while the venous system itself will screen out additional particles.

While the flow control device 40 is shown coupled directly to the arterial sheath 20 while the filter 42 is shown coupled directly to the venous sheath 24, it will be appreciated that this is merely illustrative, as the flow control device 40 and the filter 42 may be connected in any desired order. In some instances, the fluid path 34 may include the flow control device 40 but may not include the filter 42. In some instances, the fluid path 34 may include the filter 42 but may not include the flow control device 40.

In some instances, a retrograde blood flow is achieved through the arterial sheath 20 as a result of the arterial sheath 20 being fluidly coupled to the relatively high pressure of the arterial system while the vascular sheath 24 is fluidly coupled to the relatively low pressure of the venous system. In some instances, the retrograde blood flow resulting from these pressure differences means that any debris that may be knocked loose or otherwise dislodged while advancing the arterial sheath 20 through the vasculature will be carried through the fluid path 34 into the venous system. In some instances, at least some of the debris may be captured by the filter 42. The filter 42 may also capture additional debris that may be dislodged while performing various processes such as stenting the lesion 16.

Figures 3, 4:
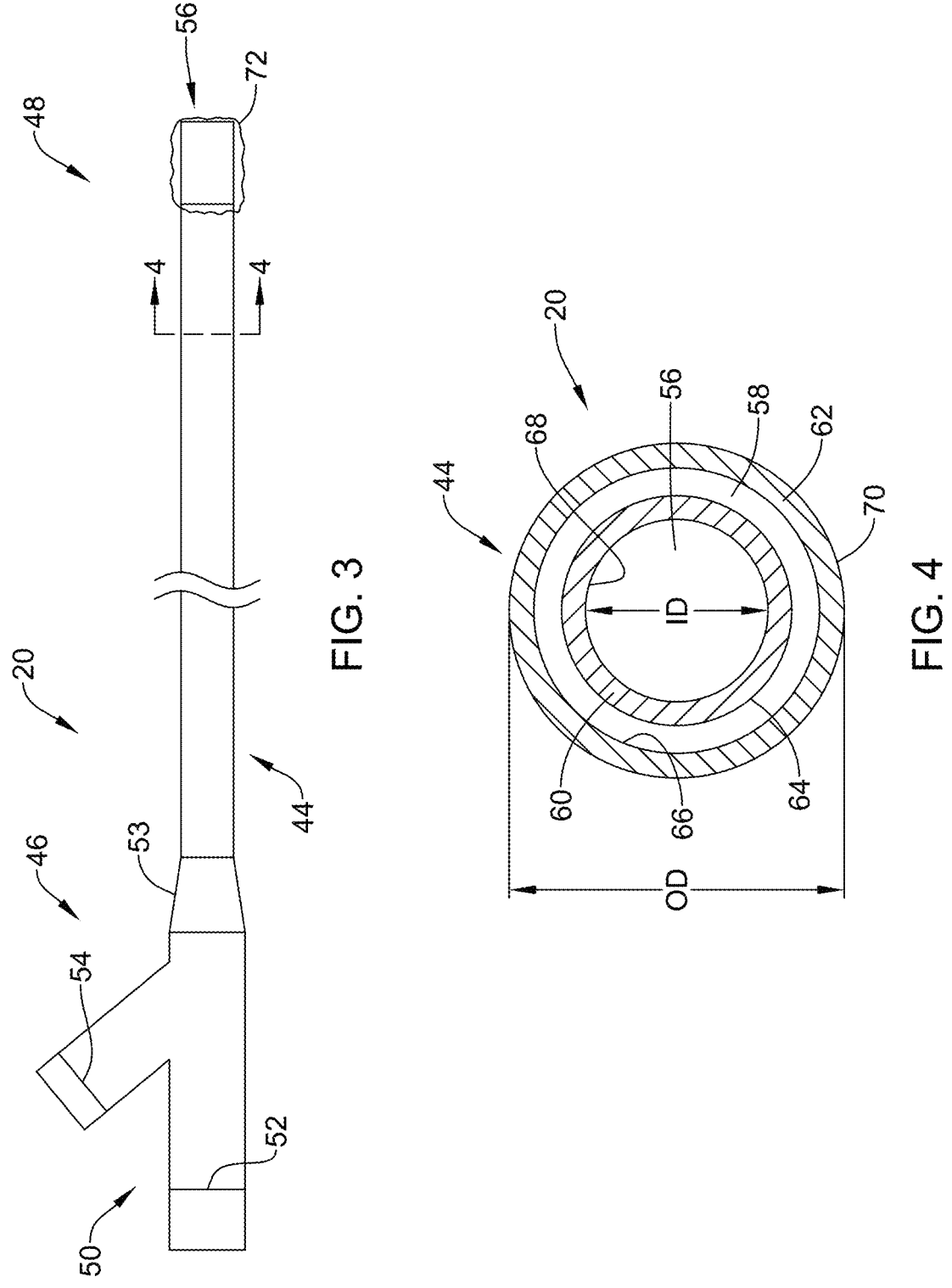
FIG. 3 is a schematic view of the illustrative arterial sheath.
FIG. 4 is a cross-sectional view taken along the line 4-4 of FIG. 3.

FIG. 3 is a schematic view of the arterial sheath 20. The arterial sheath 20 includes an elongate shaft 44 that extends from a proximal region 46 to a distal region 48. In some instances, the arterial sheath 20 may include a hub 50 that is secured relative to the proximal region 46. In some instances, the arterial sheath 20 may include a strain relief 53 extending from the hub 50 and extending a short distance distally over the elongate shaft 44. In some instances, the hub 50 may include one or more fittings such as Luer fittings. In some instances, the hub 50 may include a hemostasis valve 52 that is adapted to accommodate devices such as a guidewire, a dilator or various interventional tools therethrough. In some instances, the hemostasis valve 52 may be molded into the hub 50. In some instances, the hemostasis valve 52 may be threadedly engaged to a separate fitting formed as part of the hub 50.

In some instances, the arterial sheath 20 may include a central lumen 56 that is adapted to be accommodate a guidewire such that the arterial sheath 20 may be advanced over the guidewire. As will be discussed, the central lumen 56 may be used to accommodate retrograde blood flow through the central lumen 56 as well as to accommodate one or more interventional tools that are advanced through the central lumen. The hemostasis valve 52 may be adapted to accommodate insertion of one or more interventional tools. In some instances, the arterial sheath 20 may include an annular inflation lumen 58 (visible in FIG. 3) that is fluidly coupled with a fitting 54. The fitting 54 may be a Luer fitting, for example.

It will be appreciated that the arterial sheath 20 has several contradictory demands placed on it. The arterial sheath 20 has to have sufficient internal volume to not only accommodate interventional tools that may be advanced through the arterial sheath 20, but to also provide sufficient internal volume to accommodate retrograde blood flow through the arterial sheath 20, even with an interventional tool extending through the arterial sheath 20. The arterial sheath 20 has to accommodate these demands for internal volume while not having an outer diameter so large that it becomes problematic for being able to advance the arterial sheath 20 through the vasculature and into the common carotid artery 10. To satisfy these conflicting demands, the arterial sheath 20 has a unique construction.

FIG. 4 is a cross-sectional view of the arterial sheath 20, taken along the line 4-4 of FIG. 3. The elongate shaft 44 includes an inner shaft 60 and an outer shaft 62. In some instances, the elongate shaft 44 may vary in length, depending upon which artery is used to access the arterial system, for example. If the arterial system will be accessed via the femoral artery 18, for example, the elongate shaft 44 may have a length of at least 100 centimeters. In some instances, the elongate shaft 44 may have a length of 110 centimeters. In some instances, the elongate shaft 44 may have a length of as little as 10 centimeters. As will be appreciated, the length of the elongate shaft 44 may vary, depending at least in part upon the patient, and upon which artery is utilized to access the arterial system.

As can be seen, the annular inflation lumen 58 is formed between an outer surface 64 of the inner shaft 60 and an inner surface 66 of the outer shaft 62. In some instances, the inner shaft 60 includes a single polymeric layer, as shown. In some instances, the inner shaft 60 may include two or more polymeric layers, and may optionally include a reinforcing layer or member. In some instances, the outer shaft 62 includes a single polymeric layer, as shown, In some instances, the outer shaft 62 may include two or more polymeric layers, and may optionally include a reinforcing layer or member.

As shown, the elongate shaft 44 has an inner diameter (ID) that is defined by an inner surface 68 of the inner shaft 60 and an outer diameter (OD) that is defined by an outer surface 70 of the outer shaft 62. In some instances, the ID may be 8 French or larger, which corresponds to an ID of 2.667 millimeters (or larger). In some instances, the OD may be at least 9 French, which corresponds to an outer diameter of at least 3 millimeters. In some instances, the OD may be 9.5 French, which corresponds to an OD of 3.167 millimeters. It will be appreciated that a conversion between French size and diameter in millimeters is to divide the French size by 3. In some instances, the OD may be 10.5 French, which corresponds to an OD of 3.5 millimeters.

In some instances, the inner shaft 60 may have a wall thickness of about 0.1 millimeters. In some instances, the inner shaft 60 may have a wall thickness of about 0.004 inches (0.1016 millimeters). In some instances the outer shaft 62 may have a wall thickness of about 0.1 millimeters. In some instances, the outer shaft 62 may have a wall thickness of about 0.004 inches (0.1016 millimeters). As an example, the annular inflation lumen 58 may have an annular thickness (measured between the outer surface 64 of the inner shaft 60 and the inner surface 66 of the outer shaft 62) of 0.002 inches, or 0.00508 millimeters. As an example, the annular inflation lumen 58 may have a cross-sectional area of about 0.4 square millimeters to about 0.5 square millimeters. As another example, the annular inflation lumen 58 may have a cross-sectional area of about 0.44 square millimeters.

In some instances, the central lumen 56 may have a cross-sectional area of about 5.5 square millimeters. In some instances, the central lumen 56 may have a cross-sectional area of about 5.586 square millimeters. In some instances, at least about 40 percent of the total cross-sectional area of the central lumen 56 may remain open to accommodate retrograde blood flow even with an interventional tool having an outer diameter of about 6 French (2 millimeter diameter) remaining within the central lumen 56.

Returning briefly to FIG. 3, the arterial sheath 20 includes an inflatable balloon 72 that is secured to the elongate shaft 44 within the distal region 48 thereof. In some instances, the inflatable balloon 72 may be dimensioned to be able to, when inflated, occlude blood flow through the common carotid artery 10. An interior of the inflatable balloon 72 may be fluidly coupled with the annular inflation lumen 58 so that the inflatable balloon 72 may be inflated when desired. In some instances, the inflatable balloon 72 may be made to be as small as possible while still having sufficient dimensions to occlude the common carotid artery 10 when inflated. In some instances, the inflatable balloon 72 may be made as short (in length) as possible while still being able to oppose the vessel wall and occlude blood flow. In some instances, the inflatable balloon 72 may have an inflated diameter that is in a range of about 5 to about 13 millimeters.

Figures 5, 6:
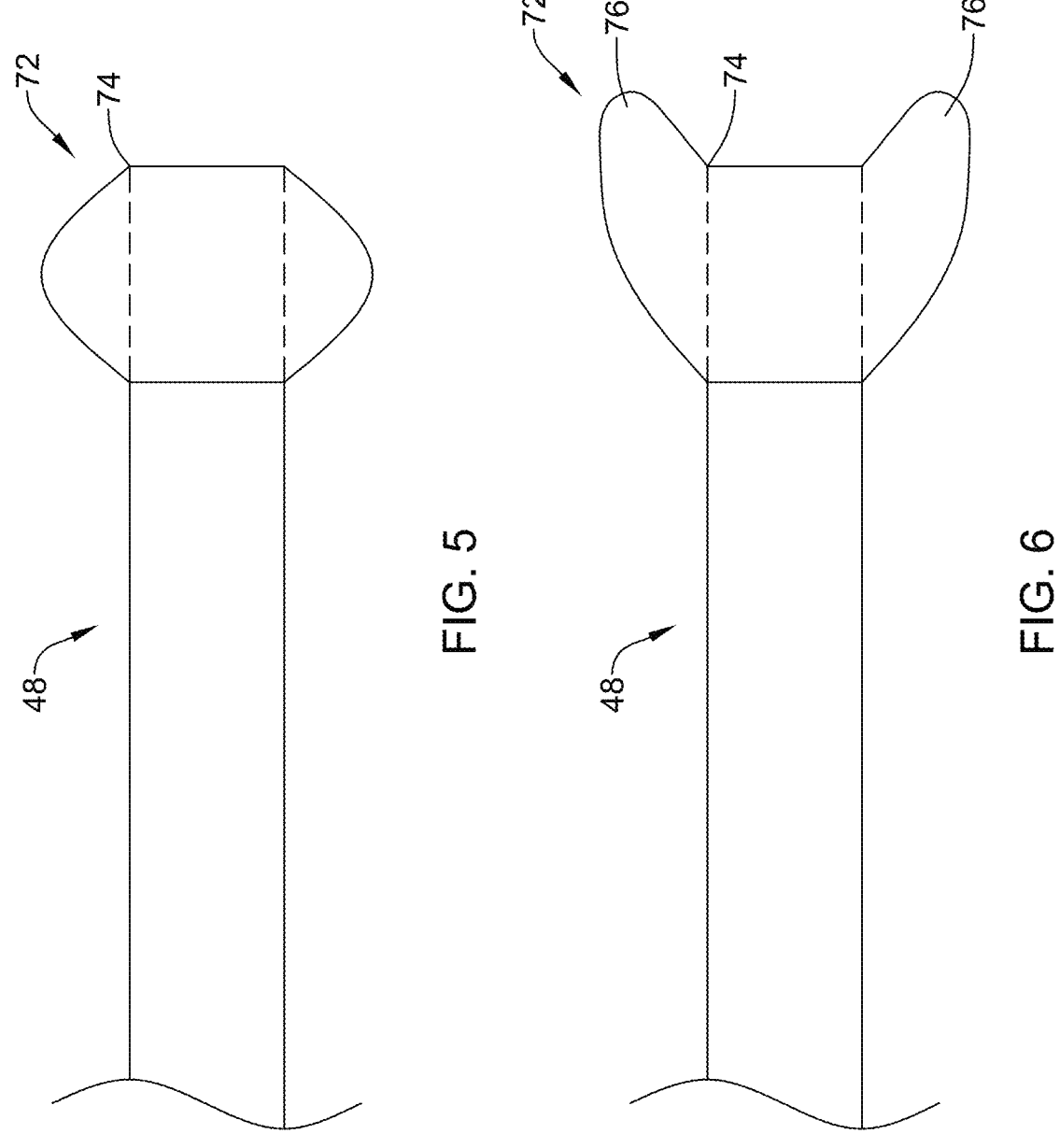
FIG. 5 is a schematic view of a distal portion of the illustrative arterial sheath of FIG. 3, showing an inflatable balloon in an inflated configuration.
FIG. 6 is a schematic view of a distal portion of the illustrative arterial sheath of FIG. 3, showing an inflatable balloon in an inflated configuration.

In some instances, the inflatable balloon 72 may be secured to the distal region 48 of the elongate shaft 44 such that when the inflatable balloon 72 is inflated, the inflatable balloon 72 extends to a distal end 74 of the elongate shaft 44. FIG. 5 provides an example of the inflatable balloon 72, when inflated, extending to the distal end 74 of the elongate shaft 44. In some instances, having the inflatable balloon 72 extending to the distal end 74 of the elongate shaft 44 means that there is less likelihood of debris becoming trapped at or near the distal end 74 of the elongate shaft 44 during retrograde blood flow through the arterial sheath 20. FIG. 6 provides an example of the inflatable balloon 72, when inflated, extending distally beyond the distal end 74 of the elongate shaft 44. In some instances, having the inflatable balloon 72 extending distally of the distal end 74 of the elongate shaft 44 means that the inflatable balloon 72, or at least wings 76 thereof, may help to function as a funnel, directing retrograde blood flow into an interior of the elongate shaft 44.

It will be appreciated that a method of providing embolic protection for carotid stenting, and perhaps other interventional techniques and processes, involves advancing the arterial sheath 20 into a patient's arterial system, where the arterial sheath 20 defines an inner lumen 56 having a cross-sectional area of at least 5 square millimeters, the arterial sheath 20 including an inflatable balloon 72. The venous sheath 24 is advanced into the patient's venous system and a fluid path 34 or connection is established between the venous sheath 24 and the arterial sheath 20. After establishing the fluid path 34, the arterial sheath 20 may be advanced through the patient's vasculature to a position within the patient's common carotid artery 10. It will be appreciated that having the fluid path 34 established between the arterial sheath 20, which is exposed to the relatively higher pressure arterial system, and the venous sheath 24, which is exposed to the relatively lower pressure venous system, will cause retrograde blood flow that will carry any debris that is dislodged while advancing the arterial sheath 20 through the vasculature to flow away from the patient's brain, where the debris may be captured in the venous system and within the filter 42.

The inflatable balloon 72 is inflated within the patient's common carotid artery 10 in order to occlude antegrade blood flow through the common carotid artery 10. Retrograde blood flow will pass through the arterial sheath 20, the venous sheath 24 and into the patient's femoral vein 26 via the fluid path 34 or connection between the arterial sheath 20 and the venous sheath 26. An interventional tool may be advanced through the central lumen 56 of the arterial sheath 20, the interventional tool having a maximum outer diameter within the central lumen 56 of the arterial sheath 20 such that at least 40 percent of the cross-sectional area of the central lumen 56 remains open for retrograde blood flow even while the interventional tool remains within the central lumen 56 of the arterial sheath 20. In some instances, if the central lumen 56 has an 8 French inner diameter, this may correspond to the interventional tool having a maximum outer diameter of 6 French.

In some instances, the central lumen 56 of the arterial sheath 20 may have a cross-sectional area of at least 5.5 square millimeters. In some instances, the interventional tool may have a maximum outer diameter within the central lumen 56 of the arterial sheath 20 of about 2 millimeters. As an example, the arterial sheath 20 may include the inner shaft 60 having an inner shaft wall thickness of about 0.004 inches (0.1016 millimeters) and the outer shaft 62 having an outer shaft wall thickness of about 0.004 inches (0.1016 millimeters). The annular inflation lumen 58 is disposed between the inner shaft 60 and the outer shaft 62, and has a cross-sectional area in a range of 0.4 square millimeters to 0.5 square millimeters.

In some instances, advancing the arterial sheath 20 through the patient's arterial system may include accessing the patient's arterial system via the patient's femoral artery 18. In some instances, advancing the venous sheath 24 into the patient's venous system may include accessing the patient's venous system via the patient's femoral vein 26. In some instances, only the patient's common carotid artery 10 is occluded when the inflatable balloon 72 is inflated. In some instances, this means that the external carotid artery 12 and the internal carotid artery 14 are not occluded as part of the method of providing embolic protection for carotid stenting.

A method of providing embolic protection for carotid stenting includes advancing the arterial sheath 20 into a patient's femoral artery 18, the arterial sheath 20 defining an inner lumen 56 having a diameter of at least 8 French (2.667 millimeters), the arterial sheath 20 including the inflatable balloon 72. The venous sheath 24 is advanced into the patient's femoral vein 26 and a fluid path or connection 34 is established between the venous sheath 24 and the arterial sheath 20. After the fluid path 34 is established, the arterial sheath 20 may be advanced through the patient's vasculature to a position within the patient's common carotid artery 10. It will be appreciated that having the fluid path 34 established between the arterial sheath 20, which is exposed to the relatively higher pressure arterial system, and the venous sheath 24, which is exposed to the relatively lower pressure venous system, will cause retrograde blood flow that will carry any debris that is dislodged while advancing the arterial sheath 20 to flow away from the patient's head, where the debris may be captured in the venous system and within the filter 42.

The inflatable balloon 72 is inflated within the patient's common carotid artery 10 in order to occlude antegrade blood flow through the patient's common carotid artery 10. Retrograde blood flow will pass through the arterial sheath 20 and the venous sheath 14 and into the patient's femoral vein 26 via the fluid path 34 or connection between the arterial sheath 20 and the venous sheath 24.

In some instances, the method may further include advancing a guidewire through the patient's femoral artery 18 and through the patient's vasculature to a position beyond the patient's common carotid artery 10. The arterial sheath 20 may be advanced over the guidewire with a dilator disposed within the arterial sheath 20 and advancing over the guidewire. In some instances, the method may further include advancing an interventional tool through the inner lumen 56 of the arterial sheath 20. In some instances, the interventional tool may have a maximum outer diameter of 6 French (2 millimeters). In some instances, establishing the fluid path 34 or connection between the venous sheath 24 and the arterial sheath 20 may include coupling the filter 42 within the fluid path 34 extending between the venous sheath 24 and the arterial sheath 20. In some instances, establishing a fluid path 34 or connection between the venous sheath 24 and the arterial sheath 20 may include coupling the flow control device 40 within the fluid path 34 extending between the venous sheath 24 and the arterial sheath 20. In some instances, the method includes occluding the patient's common carotid artery 10 without separately occluding the external carotid artery 12 or the internal carotid artery 14.

Figure 7:
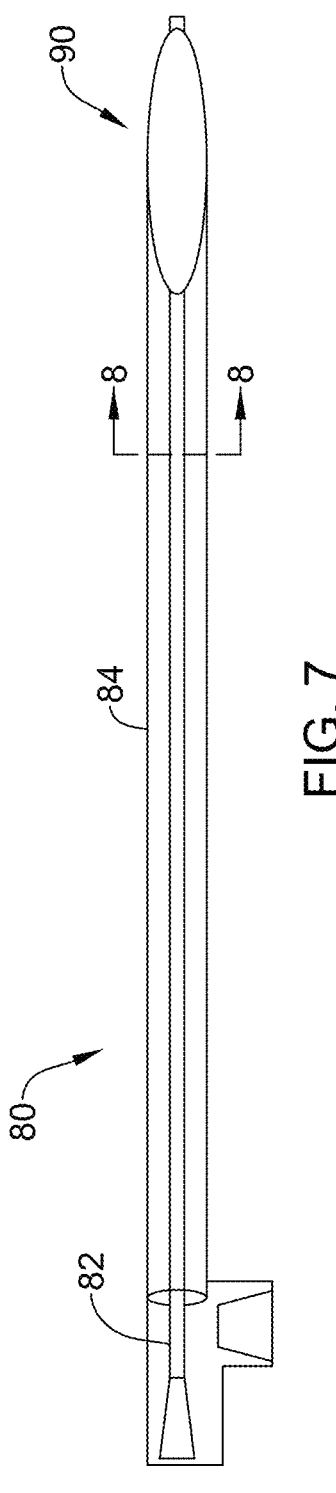
FIG. 7 is a schematic view of the illustrative arterial sheath of FIG. 3, showing its use in combination with a dilator.
Figure 8:
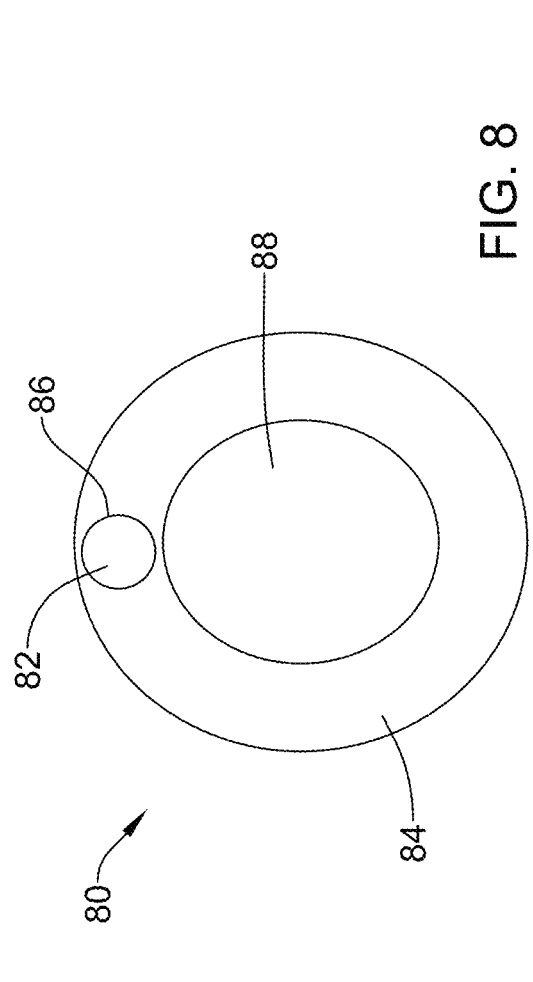
FIG. 8 is a cross-sectional view taken along the line 8-8 of FIG. 7.

Because the central lumen 56 of the arterial sheath 20 has a significant ID, in some instances a dilator may be used in advancing the arterial sheath 20 over the guidewire. FIG. 7 is a schematic view of an illustrative dilator 80 disposed over a guidewire 82 within the arterial sheath 20 and FIG. 8 is a cross-sectional view thereof, taken along the line 8-8 of FIG. 7, that may be used in delivering the arterial sheath 20. In some instances, the guidewire 82 may be a 0.035 inch guidewire, but this is just an example. In this example, the dilator 80 includes an elongate shaft 84 having an 8 French OD (2.677 millimeter diameter) with a guidewire lumen 86 that is disposed in a side wall of the elongate shaft 84. This means that a substantial lumen 88 within the elongate shaft 84 remains open. The dilator 80 includes a large mouth opening 90 to maximize blood flow while the arterial sheath 20 is advanced over the guidewire 82, with the dilator 80 disposed within the arterial sheath 20 such that the dilator 80 tracks over the guidewire 82. The large mouth opening 90 permits retrograde blood flow into the arterial sheath 20, meaning that any dislodged debris will be carried away from the patient's brain. Once a position within the patient's common carotid artery 10 is achieved, the dilator 80 may be withdrawn.

Figures 9, 10:
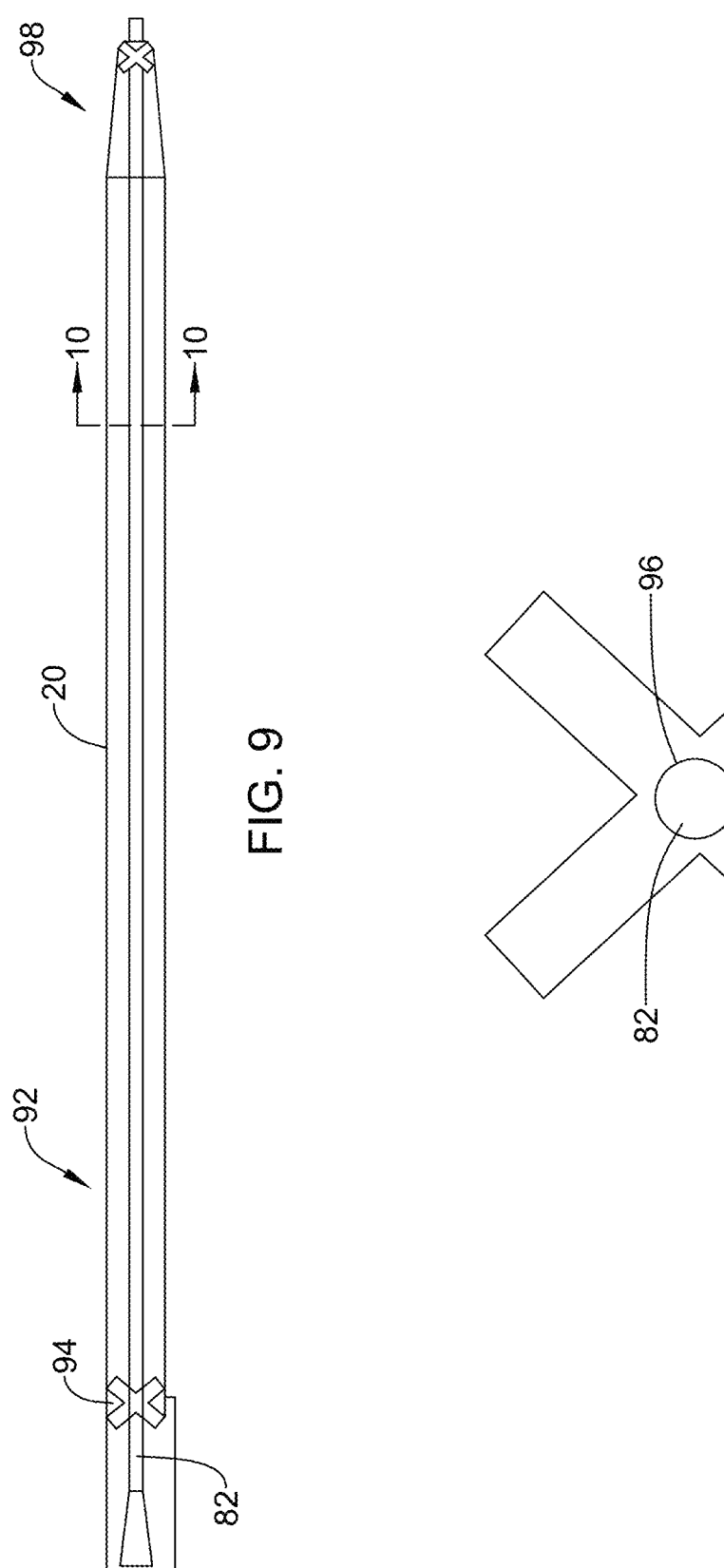
FIG. 9 is a schematic view of the illustrative arterial sheath of FIG. 3, showing its use in combination with a dilator.
FIG. 10 is a cross-sectional view taken along the line 10-10 of FIG. 7.

FIG. 9 is a schematic view of an illustrative dilator 92 that has an X-shaped cross-sectional shape 94, as seen in FIG. 10, which is a cross-sectional view taken along the line 10-10 of FIG. 9. The X-shaped cross-sectional shape 94 includes a guidewire lumen 96 extending within a center of the X-shaped cross-sectional shape 94 in order to accommodate the guidewire 82 therethrough. In some instances, the dilator 92 may have a tapered distal region 98 to facilitate advancement. The X-shaped cross-sectional shape 94 maximizes blood flow through the central lumen 56 of the arterial sheath 20 and permits retrograde blood flow into the arterial sheath 20, meaning that any dislodged debris will be carried away from the patient's brain. The arterial sheath 20 may be advanced over a guidewire with the dilator 92 disposed within the central lumen 56, with the central lumen 56 tracking over the guidewire. Once a position within the patient's common carotid artery 10 is achieved, the dilator 92 may be withdrawn.

Figures 11A, 11B, 12A, 12B, 13A, 13B:
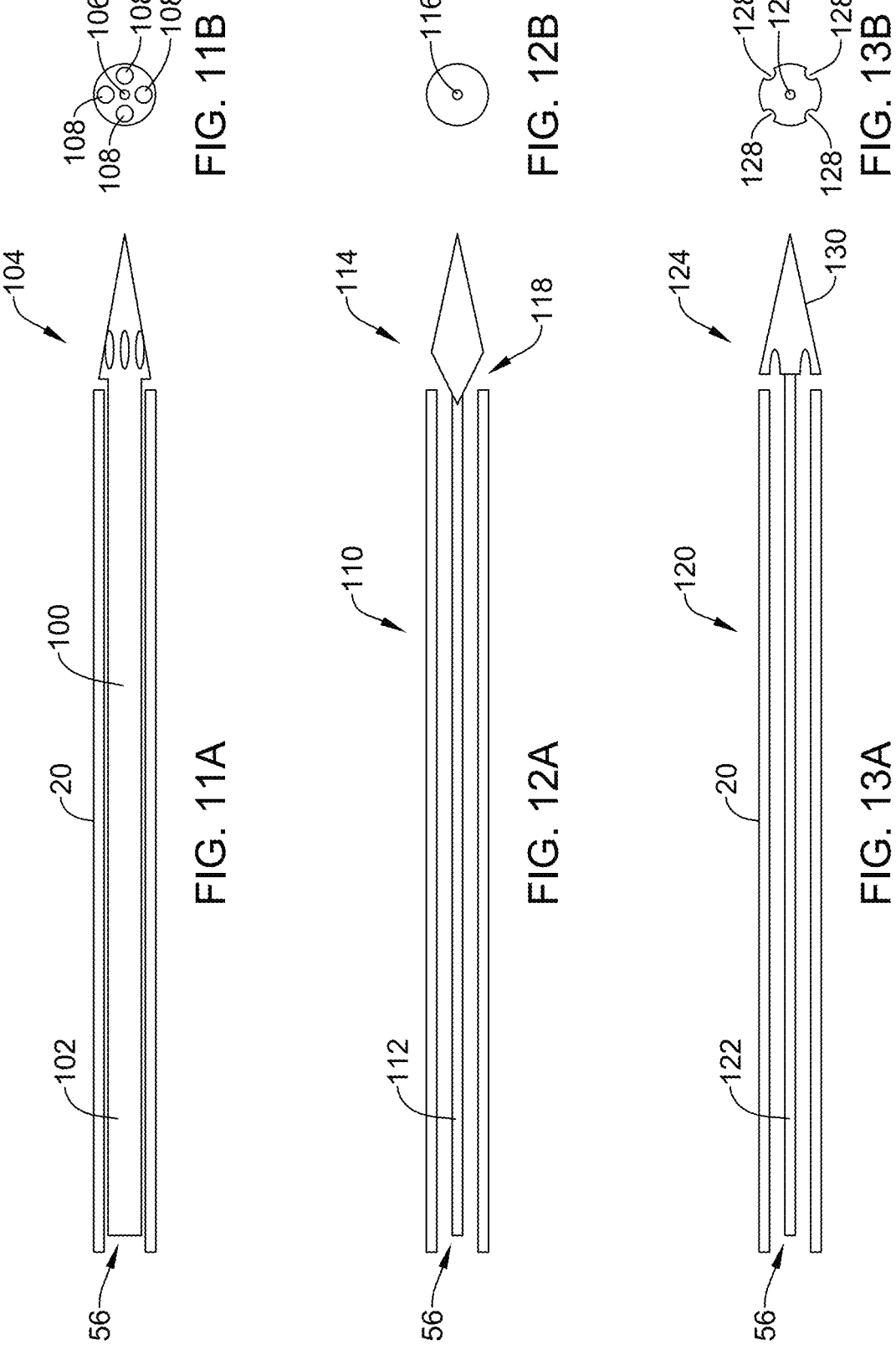
FIG. 11A is a schematic view of the illustrative arterial sheath of FIG. 3, showing its use in combination with a dilator.
FIG. 11B is a schematic end view of the dilator shown in FIG. 11A.
FIG. 12A is a schematic view of the illustrative arterial sheath of FIG. 3, showing its use in combination with a dilator.
FIG. 12B is a schematic end view of the dilator shown in FIG. 12A.
FIG. 13A is a schematic view of the illustrative arterial sheath of FIG. 3, showing its use in combination with a dilator.
FIG. 13B is a schematic end view of the dilator shown in FIG. 13A.

FIG. 11A is a schematic view of an illustrative dilator 100 disposed within the arterial sheath 20. The dilator 100 has an elongate shaft 102 that is dimensioned to fill most if not all of the central lumen 56, meaning that the arterial sheath 20 will track over a guidewire without bouncing too much from side to side. The dilator 100 has a tapered distal region 104. As seen in FIG. 11B, which is an end view of the dilator 100, the dilator 100 includes a central guidewire lumen 106 and a number of holes 108 that accommodate blood flow through the holes 108. The holes 108 enable blood to flow past the tapered distal region 104 and into the central lumen 56 of the arterial sheath 20. Retrograde blood flow through the arterial sheath 20 while the arterial sheath 20 is advanced through the vasculature means that any dislodged debris is carried away from the patient's brain, rather than flowing towards the brain. Once a position within the patient's common carotid artery 10 is achieved, the dilator 100 may be withdrawn.

FIG. 12A is a schematic view of an illustrative dilator 110 disposed within the arterial sheath 20. The dilator 110 has an elongate shaft 112. The dilator 110 has a tapered distal region 114. As seen in FIG. 12B, which is an end view of the dilator 110, the dilator 110 includes a central guidewire lumen 116. A gap 118 between the tapered distal region 114 and the arterial sheath 20 permits blood flow past the tapered distal region 114 and into the central lumen 56 of the arterial sheath 20. Retrograde blood flow through the arterial sheath 20 while the arterial sheath 20 is advanced through the vasculature means that any dislodged debris is carried away from the patient's brain, rather than flowing towards the brain. Once a position within the patient's common carotid artery 10 is achieved, the dilator 110 may be withdrawn.

FIG. 13A is a schematic view of an illustrative dilator 120 disposed within the arterial sheath 20. The dilator 120 has an elongate shaft 122. The dilator 120 has a tapered distal region 124. As seen in FIG. 13B, which is an end view of the dilator 120, the dilator 120 includes a central guidewire lumen 126. Scallops 128 formed in an outer surface 130 of the tapered distal region 124 permits blood flow past the tapered distal region 124 and into the central lumen 56 of the arterial sheath 20. Retrograde blood flow through the arterial sheath 20 while the arterial sheath 20 is advanced through the vasculature means that any dislodged debris is carried away from the patient's brain, rather than flowing towards the brain. Once a position within the patient's common carotid artery 10 is achieved, the dilator 120 may be withdrawn.

The materials that can be used for the various components of the medical devices described herein may include those commonly associated with medical devices. The medical devices described herein, as well as individual components thereof, be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-NR and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical devices described herein may also be doped with, made of, or otherwise include a radiopaque material. Radiopaque materials are understood to be materials capable of producing a relatively bright image on a fluoroscopy screen or another imaging technique during a medical procedure. This relatively bright image aids in determining a location of a medical device that includes a radiopaque material. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into various medical devices to achieve the same result.

The medical devices described herein, as well as portions and components thereof, may be made of the same material along its length, or in some embodiments, can include portions or sections made of different materials. In some embodiments, materials may be chosen to impart varying flexibility and stiffness characteristics to different portions. For example, different portions of a component, such as a proximal section and a distal section, may be formed of different materials, for example, materials having different moduli of elasticity, resulting in a difference in flexibility. In some embodiments, the material used to construct a proximal section may be relatively stiff for pushability and torqueability, and the material used to construct a distal section may be relatively flexible by comparison for better lateral trackability and steerability. For example, a proximal section may be formed of straightened 304v stainless steel wire or ribbon and a distal section may be formed of a straightened super elastic or linear elastic alloy, for example a nickel-titanium alloy wire or ribbon.

In embodiments where different portions of the medical devices described herein are made of different materials, the different portions can be connected using a suitable connecting technique and/or with a connector. For example, the different portions may be connected using welding (including laser welding), soldering, brazing, adhesive, or the like, or combinations thereof. These techniques can be utilized regardless of whether or not a connector is utilized. An example of a connector is a structure such as a hypotube or a coiled wire which has an inside diameter sized appropriately to receive and connect to the ends of the proximal portion and the distal portion.

A sheath or covering (not shown) may be disposed over portions or all of the medical devices described herein. In other embodiments, however, such a sheath or covering may be absent. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the medical devices described herein may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the medical devices described herein. Alternatively, a sheath may include a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Having thus described several illustrative embodiments of the present disclosure, those of skill in the art will readily appreciate that yet other embodiments may be made and used within the scope of the claims hereto attached. It will be understood, however, that this disclosure is, in many respects, only illustrative. Changes may be made in details, particularly in matters of shape, size, arrangement of parts, and exclusion and order of steps, without exceeding the scope of the disclosure. The disclosure's scope is, of course, defined in the language in which the appended claims are expressed.

What is claimed is:

1. A method of providing embolic protection for carotid stenting, the method comprising:
advancing an arterial sheath into a patient's arterial system, the arterial sheath defining an inner lumen having a cross-sectional area of at least 5 square millimeters, the arterial sheath including an inflatable balloon;
advancing a venous sheath into the patient's venous system;
establishing a fluid connection between the venous sheath and the arterial sheath to enable retrograde blood flow through the arterial sheath;
advancing the arterial sheath through the patient's arterial system to a position within the patient's carotid artery;
inflating the inflatable balloon within the patient's carotid artery in order to occlude antegrade blood flow therethrough; and
advancing an interventional tool through the inner lumen of the arterial sheath, the interventional tool having a maximum outer diameter within the inner lumen of the arterial sheath such that at least 40 percent of the cross-sectional area of the inner lumen remains open for retrograde blood flow even while the interventional tool remains within the inner lumen of the arterial sheath.

2. The method of claim 1, wherein the inner lumen of the arterial sheath has a cross-sectional area of at least 5.5 square millimeters.

3. The method of claim 1, wherein the maximum outer diameter of the interventional tool within the inner lumen of the arterial sheath is 2 millimeters.

4. The method of claim 1, wherein the arterial sheath comprises:
an inner shaft having an inner shaft wall thickness of about 0.1 millimeters;
an outer shaft having an outer shaft wall thickness of about 0.1 millimeters; and
an annular inflation lumen extending between the inner shaft and the outer shaft, the annular inflation lumen having a cross-sectional area in a range of 0.4 square millimeters to 0.5 square millimeters.

5. The method of claim 1, wherein advancing the arterial sheath into the patient's arterial system comprises accessing the patient's arterial system via the patient's femoral artery.

6. The method of claim 1, wherein advancing the venous access sheath into the patient's venous system comprises accessing the patient's venous system via the patient's femoral vein.

7. The method of claim 1, wherein inflating the inflatable balloon within the patient's carotid artery comprises inflating the inflatable balloon within the patient's common carotid artery.

8. The method of claim 7, wherein only the patient's common carotid artery is occluded.

9. A method of providing embolic protection for carotid stenting, the method comprising:
advancing an arterial sheath into a patient's femoral artery, the arterial sheath defining an inner lumen having a diameter of at least 8 French, the arterial sheath including an inflatable balloon;

advancing a venous sheath into the patient's femoral vein;

establishing a fluid connection between the venous sheath and the arterial sheath to enable retrograde blood flow through the arterial sheath;

advancing the arterial sheath through the patient's vasculature to a position proximate the patient's common carotid artery;

inflating the inflatable balloon within the patient's common carotid artery in order to occlude antegrade blood flow through the patient's common carotid artery; and advancing an interventional tool having a maximum outer diameter of 6 French through the inner lumen of the arterial sheath.

10. The method of claim 9, further comprising:

advancing a guidewire through the patient's femoral artery and through the patient's vasculature to a position beyond the patient's common carotid artery;

wherein advancing the arterial sheath through the patient's vasculature to a position proximate the patient's common carotid artery comprises advancing the arterial sheath over the guidewire with a dilator disposed within the arterial sheath and advancing over the guidewire.

11. The method of claim 9, wherein establishing a fluid connection between the venous sheath and the arterial sheath comprises coupling a filter within a fluid path extending between the venous sheath and the arterial sheath.

12. The method of claim 9, wherein establishing a fluid connection between the venous sheath and the arterial sheath comprises coupling a flow control device within a fluid path extending between the venous sheath and the arterial sheath.

13. The method of claim 9, comprising occluding the patient's common carotid artery without separately occluding the external carotid artery or the internal carotid artery.

14. The method of claim 9, wherein the arterial sheath comprises:

an inner shaft having an inner shaft wall thickness of about 0.1 millimeters;

an outer shaft having an outer sheath wall thickness of about 0.1 millimeters; and an annular inflation lumen extending between the inner shaft and the outer shaft, the annular inflation lumen having a cross-sectional area in a range of 0.4 square millimeters to 0.5 square millimeters.

15. A method of providing embolic protection for carotid stenting, the method comprising:

advancing an arterial sheath into a patient's femoral artery, the arterial sheath defining an inner lumen having a diameter of at least 8 French, the arterial sheath including an inflatable balloon;

wherein the arterial sheath comprises:

an inner shaft having an inner shaft wall thickness of about 0.1 millimeters;

an outer shaft having an outer sheath wall thickness of about 0.1 millimeters; and an annular inflation lumen extending between the inner shaft and the outer shaft, the annular inflation lumen having a cross-sectional area in a range of 0.4 square millimeters to 0.5 square millimeters;

advancing a venous sheath into the patient's femoral vein;

establishing a fluid connection between the venous sheath and the arterial sheath to enable retrograde blood flow through the arterial sheath;

advancing the arterial sheath through the patient's vasculature to a position proximate the patient's common carotid artery; and inflating the inflatable balloon within the patient's common carotid artery in order to occlude antegrade blood flow through the patient's common carotid artery.

* * * * *